(12) United States Patent
Ricci et al.

(10) Patent No.: US 10,231,769 B2
(45) Date of Patent: Mar. 19, 2019

(54) APPARATUS, SYSTEM, AND METHOD FOR PASSING CABLE THROUGH A PASS-THROUGH HOLE IN BONE

(71) Applicant: Cable Fix LLC, Hernando, MS (US)

(72) Inventors: William Ricci, Richmond Heights, MO (US); Carey Bryant, Hernando, MS (US); Mark Brinker, Houston, TX (US)

(73) Assignee: CABLE FIX LLC, Hernando, MS (US)

( * ) Notice: Subject to any disclaimer, the term of this patent is extended or adjusted under 35 U.S.C. 154(b) by 661 days.

(21) Appl. No.: 14/961,415

(22) Filed: Dec. 7, 2015

(65) Prior Publication Data

US 2017/0156738 A1 Jun. 8, 2017

(51) Int. Cl.
*A61B 17/00* (2006.01)
*A61B 17/88* (2006.01)
*A61B 17/16* (2006.01)

(52) U.S. Cl.
CPC ...... *A61B 17/8861* (2013.01); *A61B 17/1615* (2013.01)

(58) Field of Classification Search
CPC combination set(s) only.
See application file for complete search history.

(56) References Cited

U.S. PATENT DOCUMENTS

| | | |
|---|---|---|
| 479,938 A | 8/1892 | Fredlihp |
| 899,612 A | 9/1908 | Phillips |
| 3,166,072 A | 1/1965 | Sullivan, Jr. |
| 4,060,089 A | 11/1977 | Noiles |
| 4,532,927 A | 8/1985 | Miksza, Jr. |
| 4,534,350 A | 8/1985 | Golden et al. |
| 4,534,352 A | 8/1985 | Korthoff |
| 4,548,202 A | 10/1985 | Duncan |
| 4,573,469 A | 3/1986 | Golden et al. |
| 4,610,250 A | 9/1986 | Green |
| 4,754,758 A | 7/1988 | Lehmann |
| 4,932,960 A | 6/1990 | Green |
| 5,358,510 A | 10/1994 | Luscombe et al. |
| 5,478,353 A | 12/1995 | Yoon |
| 5,620,452 A | 4/1997 | Yoon |
| 5,665,109 A | 9/1997 | Yoon |
| 5,797,932 A | 8/1998 | Min et al. |
| 5,984,001 A | 11/1999 | Larsen et al. |
| 6,276,032 B1 | 8/2001 | Nortman et al. |
| 6,712,830 B2 | 3/2004 | Esplin |
| 6,966,919 B2 | 11/2005 | Sixto et al. |
| 7,033,378 B2 | 4/2006 | Smith et al. |
| 7,094,251 B2 | 8/2006 | Bonutti et al. |
| 7,678,122 B2 | 3/2010 | Kortenbach et al. |

(Continued)

*Primary Examiner* — Sameh Boles
(74) *Attorney, Agent, or Firm* — Kunzler, PC (57) ABSTRACT

An apparatus for passing a cable through a pass-through hole in a bone that includes a hole-forming tool and a cable. The hole-forming tool has a shank, a cutting portion, and a first connection feature. The cutting portion is interposed between the shank and the first connection feature and the shank is detachably coupleable to a driving tool. The cable has a first-end portion that has a second connection feature. The cable is detachably coupleable to the hole-forming tool via the first connection feature of the hole-forming tool and the second connection feature of the first-end portion of the cable.

15 Claims, 8 Drawing Sheets

(56) References Cited

U.S. PATENT DOCUMENTS

| | | |
|---|---|---|
| 7,854,750 B2 | 12/2010 | Bonutti et al. |
| 7,985,241 B2 | 7/2011 | Smith et al. |
| 8,080,020 B2 | 12/2011 | Kortenbach et al. |
| 8,114,100 B2 | 2/2012 | Smith et al. |
| 8,162,977 B2 | 4/2012 | Bonutti et al. |
| 8,454,628 B2 | 6/2013 | Smith et al. |
| 8,613,750 B2 | 12/2013 | Smith et al. |
| 9,039,596 B2 | 5/2015 | Sater |
| 9,220,503 B2 | 12/2015 | Ranchod |
| 9,788,827 B2 | 10/2017 | Miksza et al. |
| 2001/0051815 A1 | 12/2001 | Esplin |
| 2002/0029044 A1 | 3/2002 | Monassevitch et al. |
| 2004/0044366 A1 | 3/2004 | Bonutti et al. |
| 2004/0059349 A1 | 3/2004 | Sixto et al. |
| 2004/0059354 A1 | 3/2004 | Smith et al. |
| 2004/0059358 A1 | 3/2004 | Kortenbach et al. |
| 2007/0032825 A1 | 2/2007 | Bonutti et al. |
| 2008/0046007 A1 | 2/2008 | Schwemberger et al. |
| 2008/0046008 A1 | 2/2008 | Smith et al. |
| 2008/0097430 A1* | 4/2008 | Bernstein ........... A61B 17/1764 606/60 |
| 2008/0108897 A1 | 5/2008 | Bonutti et al. |
| 2008/0140095 A1 | 6/2008 | Smith et al. |
| 2008/0147116 A1 | 6/2008 | Smith et al. |
| 2008/0149685 A1 | 6/2008 | Smith et al. |
| 2010/0179568 A1 | 7/2010 | Kortenbach et al. |
| 2010/0198258 A1 | 8/2010 | Heaven et al. |
| 2011/0040307 A1 | 2/2011 | Ranchod |
| 2011/0092993 A1 | 4/2011 | Jacobs |
| 2011/0201877 A1 | 8/2011 | Sater |
| 2012/0065638 A1 | 5/2012 | Moore |
| 2012/0130374 A1 | 5/2012 | Bouduban et al. |
| 2012/0143247 A1 | 6/2012 | Smith et al. |
| 2016/0081686 A1 | 3/2016 | Miksza et al. |
| 2016/0100835 A1 | 4/2016 | Linder et al. |
| 2016/0346023 A1 | 12/2016 | Bouduban et al. |
| 2017/0156771 A1 | 6/2017 | Brinker et al. |
| 2017/0156772 A1 | 6/2017 | Brinker et al. |
| 2017/0156774 A1 | 6/2017 | Bryant et al. |
| 2017/0156775 A1 | 6/2017 | Bryant et al. |
| 2017/0156779 A1 | 6/2017 | Bryant et al. |
| 2017/0156847 A1 | 6/2017 | Ricci et al. |
| 2018/0055550 A1 | 3/2018 | Bryant et al. |

\* cited by examiner

APPARATUS, SYSTEM, AND METHOD FOR PASSING CABLE THROUGH A PASS-THROUGH HOLE IN BONE

FIELD

The subject matter of the present disclosure relates generally to passing cable through a pass-through hole (e.g., tunnel) in bone. More specifically, the present disclosure relates to pulling cable through a pass-through hole in bone using a hole-forming tool.

BACKGROUND

Various medical procedures utilize cables or conventional sutures to secure damaged skeletal tissue or soft tissue. Tissues, such as bones or soft-tissues, that have been fragmented, fractured, broken, torn, pulled, stretched, or otherwise damaged need to be set and held in specific orientations in order to properly heal. Cables or conventional sutures may be useful for securing/attaching torn tissue back together or for facilitating holding bone fragments in place. For example, cerclage cables or conventional sutures can be wrapped around or lie adjacent to bone for fracture reduction, fracture fixation, and crack propagation prevention. However, conventional tools and procedures for utilizing cables or conventional sutures in medical surgeries are generally time-consuming, complex, and usually involve multiple in-situ steps that are difficult to perform.

SUMMARY

From the foregoing discussion, it should be apparent that a need exists for an apparatus, system, and method for fracture reduction, fracture fixation, and crack propagation prevention that overcome the limitations of conventional medical tools and procedures. Beneficially, such an apparatus, system, and method would improve the ease, efficiency, and effectiveness of these and other medical procedures.

The subject matter of the present application has been developed in response to the present state of the art, and in particular, in response to the problems and needs in the art that have not yet been fully solved by currently available medical tools and procedures. For example, the ease, efficiency, and effectiveness of fracture reduction, fracture fixation, and crack propagation prevention is improved by passing cable through a pass-through hole (e.g., a tunnel) in bone with a hole-forming tool used to form the hole in the bone. Once the cable is passed through the bone, the cable may be tensioned to reduce and/or secure the fracture, dislocation, or subluxation, or to secure torn soft tissues to bone. Accordingly, the present disclosure has been developed to provide an apparatus for passing cable through a hole/tunnel in bone, and its related systems and methods, that overcome many or all of the above-discussed shortcomings in the art.

Disclosed herein is one embodiment of an apparatus for passing a cable through a pass-through hole in a bone. The apparatus includes a hole-forming tool having a shank, a cutting portion, and a first connection feature. The cutting portion is interposed between the shank and the first connection feature and the shank is detachably coupleable to a driving tool. The apparatus also includes a cable that has a first-end portion. The first end-portion of the cable has a second connection feature and the cable is detachably coupleable to the hole-forming tool via the first connection feature of the hole-forming tool and the second connection feature of the first-end portion of the cable.

According to one implementation, the apparatus further includes a coupler having a proximal-end portion and a distal-end portion. The proximal-end portion has a third connection feature and the distal-end portion has a fourth connection feature. The hole-forming tool is detachably coupleable to the proximal-end portion of the coupler via engagement between the first and third connection features and the distal-end portion of the coupler is detachably coupleable to the cable via engagement between the second and fourth connection features. In such an implementation, the cutting portion of the hole-forming tool is a first cutting portion and the hole-forming tool may include a second cutting portion. The first connection feature is interposed between the first cutting portion and the second cutting portion. Also, a diameter of the first cutting portion of the hole-forming tool may be comparatively larger than a diameter of the second cutting portion of the hole-forming tool.

In one implementation, the diameter of the first cutting portion of the hole-forming tool is larger than a diameter of the coupler. In another implementation, the second cutting portion of the hole-forming tool is a cutting tip. In yet another implementation, the first connection feature of the hole-forming tool has externally facing threads and the third connection feature of the coupler has internally facing threads. The internally facing threads of the third connection feature are threadably engageable with the externally facing threads of the first connection feature.

In one implementation, the second connection feature of the first-end portion of the cable has a non-threaded protrusion and the fourth connection feature of the distal-end portion of the coupler has a non-threaded cavity. The non-threaded protrusion of the second connection feature may be configured to be received into the non-threaded cavity of the fourth connection feature via an interference fit. In another implementation, the second-end portion of the cable has a retainer feature configured to prevent the second-end portion of the cable from passing through the pass-through hole in the bone.

According to one implementation, the apparatus further includes a shank connection feature interposed between the proximal connection feature and the cutting portion. In such an implementation, the second connection feature of the first-end portion of the cable is detachably coupleable to the hole-forming tool via one of the first connection feature and the shank connection feature. The apparatus may further include a coupler having a proximal-end portion and a distal-end portion. The proximal-end portion has a third connection feature and the distal-end portion has a fourth connection feature. The hole-forming tool is detachably coupleable to the proximal-end portion of the coupler via engagement between the third connection feature and one of the first connection feature and the shank connection feature. The distal-end portion of the coupler is detachably coupleable to the cable via engagement between the second and fourth connection features.

In one implementation, the cutting portion of the hole-forming tool is a first cutting portion and the hole-forming tool has a second cutting portion. The first connection feature is interposed between the first cutting portion and the second cutting portion. Also, the diameter of the first cutting portion of the hole-forming tool may be comparatively larger than a diameter of the second cutting portion of the hole-forming tool. In such an implementation, the diameter of the first cutting portion of the hole-forming tool is larger than a diameter of the coupler.

In one implementation, the first connection feature and the shank connection feature of the hole-forming tool have externally facing threads while the third connection feature of the coupler has complementary internally facing threads. In another implementation, the second connection feature of the first-end portion of the cable includes a non-threaded protrusion and the fourth connection feature of the distal-end portion of the coupler has a non-threaded cavity. The non-threaded protrusion of the second connection feature is configured to be received into the non-threaded cavity of the fourth connection feature via an interference fit.

Also disclosed herein is one embodiment of a method for passing a cable through bone. The method includes driving a hole-forming tool through a bone in a first direction to form a pass-through hole extending from a first side of the bone to a second side of the bone until at least a first connection feature of the hole-forming tool protrudes from the pass-through hole on the second side of the bone. The method further includes subsequently coupling a cable to the hole-forming tool via the first connection feature of the hole-forming tool and a second connection feature of the cable and then withdrawing the hole-forming tool from the pass-through hole in a second direction opposite the first direction to pull the cable through the pass-through hole such that at least a portion of the cable protrudes from the first side of the bone.

According to certain implementations, the method includes tensioning the cable to a measurable and adjustable tension, with the cable positioned in the pass-through hole, to cause a measurable and adjustable compression of the bone by the cable. In one implementation, coupling the cable to the hole-forming tool includes coupling the hole-forming tool directly to a coupler via engagement between the first connection feature of the hole-forming tool and a third connection feature of a proximal-end portion of the coupler and also coupling the coupler directly to the cable via engagement between a fourth connection feature of a distal-end portion of the coupler and the second connection feature of the first-end portion of the cable. In another implementation, the step of withdrawing the hole-forming tool from the pass-through hole includes engaging a retainer feature of the second-end portion of the cable with an opening of the pass-through hole on the second side of the bone. In such an implementation, the diameter of the retainer feature is larger than a diameter of the pass-through hole. In another implementation, driving the hole-forming tool includes cutting the bone with a first cutting portion of the hole-forming tool and a second cutting portion of the hole-forming tool, with the second cutting portion forming a pilot hole for the first cutting portion.

Also disclosed herein is another embodiment of a method for passing a cable through bone. The method includes driving a hole-forming tool through a bone in a first direction to form a pass-through hole extending from a first side of the bone to a second side of the bone, leaving at least a shank connection feature of the hole-forming tool protruding from the pass-through hole on the first side of the bone. The method subsequently includes coupling a cable to the hole-forming tool via the shank connection feature of the hole-forming tool and a second connection feature of the cable and then withdrawing the hole-forming tool from the pass-through hole in the first direction to pull the cable through the pass-through hole such that at least a portion of the cable protrudes from the second side of the bone.

According to certain implementations, the method includes tensioning the cable to a measurable and adjustable tension, with the cable positioned in the pass-through hole, to cause a measurable and adjustable compression of the bone by the cable. In one implementation, coupling the cable to the hole-forming tool includes coupling the hole-forming tool directly to a coupler via engagement between the shank connection feature of the hole-forming tool and a third connection feature of a proximal-end portion of the coupler and coupling the coupler directly to the cable via engagement between a fourth connection feature of a distal-end portion of the coupler and the second connection feature of the first-end portion of the cable. In another implementation, withdrawing the hole-forming tool from the pass-through hole includes engaging a retainer feature of the second-end portion of the cable with an opening of the pass-through hole on the first side of the bone. In such an implementation, the diameter of the retainer feature is larger than a diameter of the pass-through hole.

Reference throughout this specification to features, advantages, or similar language does not imply that all of the features and advantages that may be realized with the present disclosure should be or are in any single embodiment of the disclosure. Rather, language referring to the features and advantages is understood to mean that a specific feature, advantage, or characteristic described in connection with an embodiment is included in at least one embodiment of the subject matter disclosed herein. Thus, discussion of the features and advantages, and similar language, throughout this specification may, but do not necessarily, refer to the same embodiment.

Furthermore, the described features, advantages, and characteristics of the disclosure may be combined in any suitable manner in one or more embodiments. One skilled in the relevant art will recognize that the subject matter of the present application may be practiced without one or more of the specific features or advantages of a particular embodiment. In other instances, additional features and advantages may be recognized in certain embodiments that may not be present in all embodiments of the disclosure. Further, in some instances, well-known structures, materials, or operations are not shown or described in detail to avoid obscuring aspects of the subject matter of the present disclosure. These features and advantages of the present disclosure will become more fully apparent from the following description and appended claims, or may be learned by the practice of the disclosure as set forth hereinafter.

BRIEF DESCRIPTION OF THE DRAWINGS

In order that the advantages of the disclosure will be readily understood, a more particular description of the disclosure briefly described above will be rendered by reference to specific embodiments that are illustrated in the appended drawings. Understanding that these drawings depict only typical embodiments of the disclosure and are not therefore to be considered to be limiting of its scope, the subject matter of the present application will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment of the present disclosure. Thus, appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

In the following description, numerous specific details are provided. One skilled in the relevant art will recognize, however, that the subject matter of the present application may be practiced without one or more of the specific details, or with other methods, components, materials, and so forth. In other instances, well-known structures, materials, or operations are not shown or described in detail to avoid obscuring aspects of the disclosure. Also, like reference numbers (e.g., 121 and 221) refer to like components (e.g., different embodiments of the same component).

Illustrated in FIGS. 1A-5B are several representative embodiments of an apparatus 100 for passing cable through bone. As described herein, the apparatus for passing cable through bone provides various advantages and benefits over other medical tools and procedures. However, the recited advantages are not meant to be limiting in any way, as one skilled in the art will appreciate that other advantages may also be realized upon practicing the present disclosure.

Figures 1A, 1B:
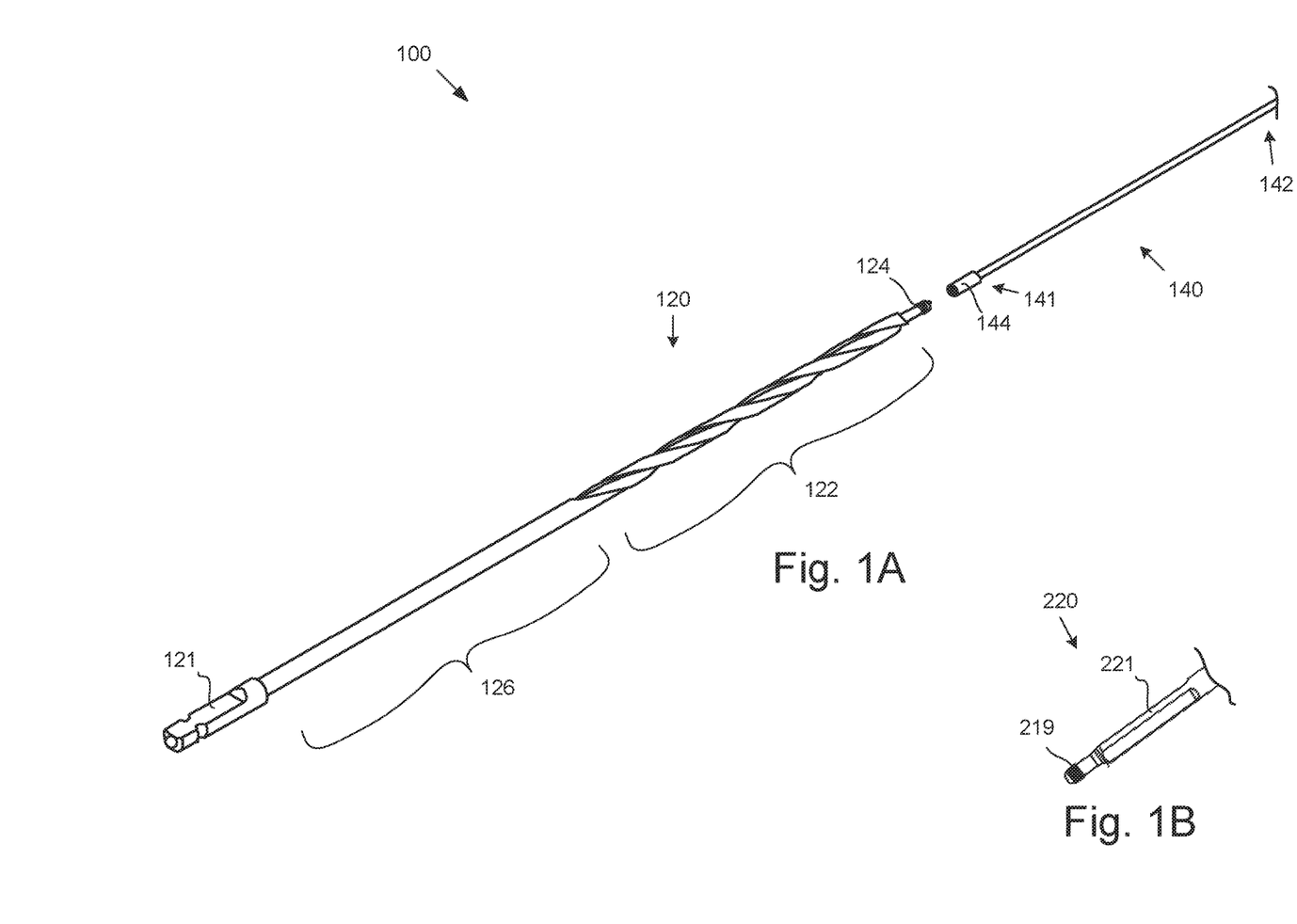
FIG. 1A is an exploded perspective view of an apparatus for passing cable through a pass-through hole (e.g., a tunnel) in bone, with a first connection feature of a hole-forming tool being coupleable with a cable, according to one embodiment.
FIG. 1B is a partial perspective view of the apparatus, showing the hole-forming tool having a shank connection feature that is coupleable with the cable, according to one embodiment.

FIG. 1A is an exploded perspective view of the apparatus 100 for passing cable through a pass-through hole (e.g., a tunnel) in bone. The apparatus 100 includes a hole-forming tool 120 and a cable 140 coupleable to the hole-forming tool 120. Generally, the hole-forming tool 120 facilitates the formation of a pass-through hole in a bone. As defined herein, the hole-forming tool 120 is any type of tool or device that can be used to form a hole in bone, such as, for example, a drilling tool (e.g., drill bit), a reaming tool, a cutting tool, or the like. Once the pass-through hole has been formed, the practitioner can couple the cable 140 to the hole-forming tool and pull the hole-forming tool and cable through the hole. The apparatus 100 eliminates the need to use both a drilling tool and a cable-passing tool.

The hole-forming tool 120 has a shank 121, a cutting portion 122, and a first connection feature 124. The cutting portion 122 is interposed between the shank 121 and the first connection feature 124. In one embodiment, as shown in FIG. 1A, the hole-forming tool 120 includes a non-cutting portion 126 interposed between the shank 121 and the cutting portion 122. In another embodiment, the cutting portion 122 extends substantially along an entire length between the shank 121 and the first connection feature 124. The shank 121 is detachably coupleable to a driving tool, such as a power drill. The cable 140 has a first-end portion 141 and a second-end portion 142. The first-end portion 141 of the cable 140 has a second connection feature 144. The hole-forming tool 120 is coupleable to the cable 140 via the respective first and second connection features 124, 144. According to the embodiment shown in FIG. 1A, the hole-forming tool 120 can be directly coupled to the cable 140 via direct engagement between the first and the second connection features 124, 144. However, in an alternative embodiment, a coupler 160 may be interposed between the hole-forming tool 120 and the cable 140 to facilitate the connection between the hole-forming tool 120 and the cable 140, as described in greater detail below with reference to FIG. 4. The coupler 160 has a proximal-end portion 161 and a distal-end portion 162. The proximal-end portion 161 has a third connection feature 164 and the distal-end portion 162 has a fourth connection feature 166.

FIG. 1B is a partial perspective view of another embodiment of a hole-forming tool 220. According to the embodiment shown in FIG. 1B, the shank 221 of the hole-forming tool 220 has a shank connection feature 219 that is also coupleable with the cable 140 via the second connection feature 144. In other words, FIG. 1B shows an alternative shank 221 that may be implemented with the apparatus 100 depicted in FIG. 1A (i.e., shank 221 replaces shank 121). The shank 221 is interposed between the shank connection feature 219 and the cutting portion 122. In such an implementation, as will be described in greater detail below with reference to FIGS. 3A and 3B, the cable 140 may be coupled to the hole-forming tool on either end, thus allowing the cable to be pulled through the bone in either direction.

The hole-forming tool 120 may be made from stainless steel or titanium. In another embodiment, the hole-forming tool 120 may be made from low carbon steel, high carbon steel, high speed steel, cobalt steel alloys, tungsten carbide, and polycrystalline diamond, among other materials. The hole-forming tool 120 may also have one or more coatings to prevent corrosion, or improve the cutting performance of the hole-forming tool 120. The coating, which may be antimicrobial, may also be useful to decrease the likelihood of toxicity and infection in the bone tissue.

The shank 121 may be shaped and configured according to a specific chuck of a drilling tool. For example, the shank 121 may have a non-circular outer-periphery that can be received within a complimentary non-circular inner surface of a drill. In another embodiment, the shank may have a polygonal outer-periphery. In yet another embodiment, the shank may be cylindrical and the chuck of the drill may have sufficient clamping power to securely hold the shank and induce rotation of the hole-forming tool. The spiral, point angle, lip angle, and length of the cutting portion 122 of the hole-forming tool 120 may be selected according to the specifics of a given surgical procedure.

As defined herein, the term "cable" refers to a cord-like element, such as a wire, filament, weave, or thread, whether bundled or individual, that is capable of holding a measurable and adjustable tension and causing a measurable and adjustable compression of bone. In other words, the tension in the cable can be measured, such as by a tension measuring device, and can be adjusted, such as after an initial tensioning of the cable. When used to compress bone (e.g., to compress two bone segments together), the measured tension in the cable is equal to a measured compression of the bone. Thus, as used herein, a measured and adjustable tension of a cable is synonymous with a measured and adjustable compression of bone by the cable.

In one embodiment, the measurable and adjustable tension may be a specific, known, predictable, expected, controllable, anticipated, desired, repeatable, sustainable, and/or predeterminable tension. For example, the cable 140 may be passed through a pass-through hole in a bone and may be tensioned to a measurable and adjustable tension in order to facilitate the reduction and fixation of fractures or to otherwise facilitate the repair of dislocations or soft-tissue damage. In other words, the cable 140 is not a conventional suture or conventional thread material, since such materials are incapable of, or at least not well-suited for, maintaining a measurable and adjustable tension. Thus, the term "cable" refers to a flexible yet substantially non-stretchable element that can be tensioned to a measurable and adjustable tension. Because the cable 140 is capable of maintaining or retaining a measurable and adjustable tension, the effectiveness and reproducibility of successful surgical procedures is improved. In other words, different surgical procedures relating to different bones in the body may involve different degrees of retention/fixation force (e.g., the fixation force required to reduce a fracture in the femur may be greater than the fixation force required to reduce a fracture in the patella). Accordingly, the ability of the cable 140 to be tensioned to a measurable and adjustable tension improves the reliability and reproducibility of surgical procedures when compared with other medical procedures that do not utilize cables. The cable 140 may be made from any one of various materials. For example, in specific implementations, the cable 140 is made from metal, such as stainless steel, titanium, or other metal.

Figure 2:
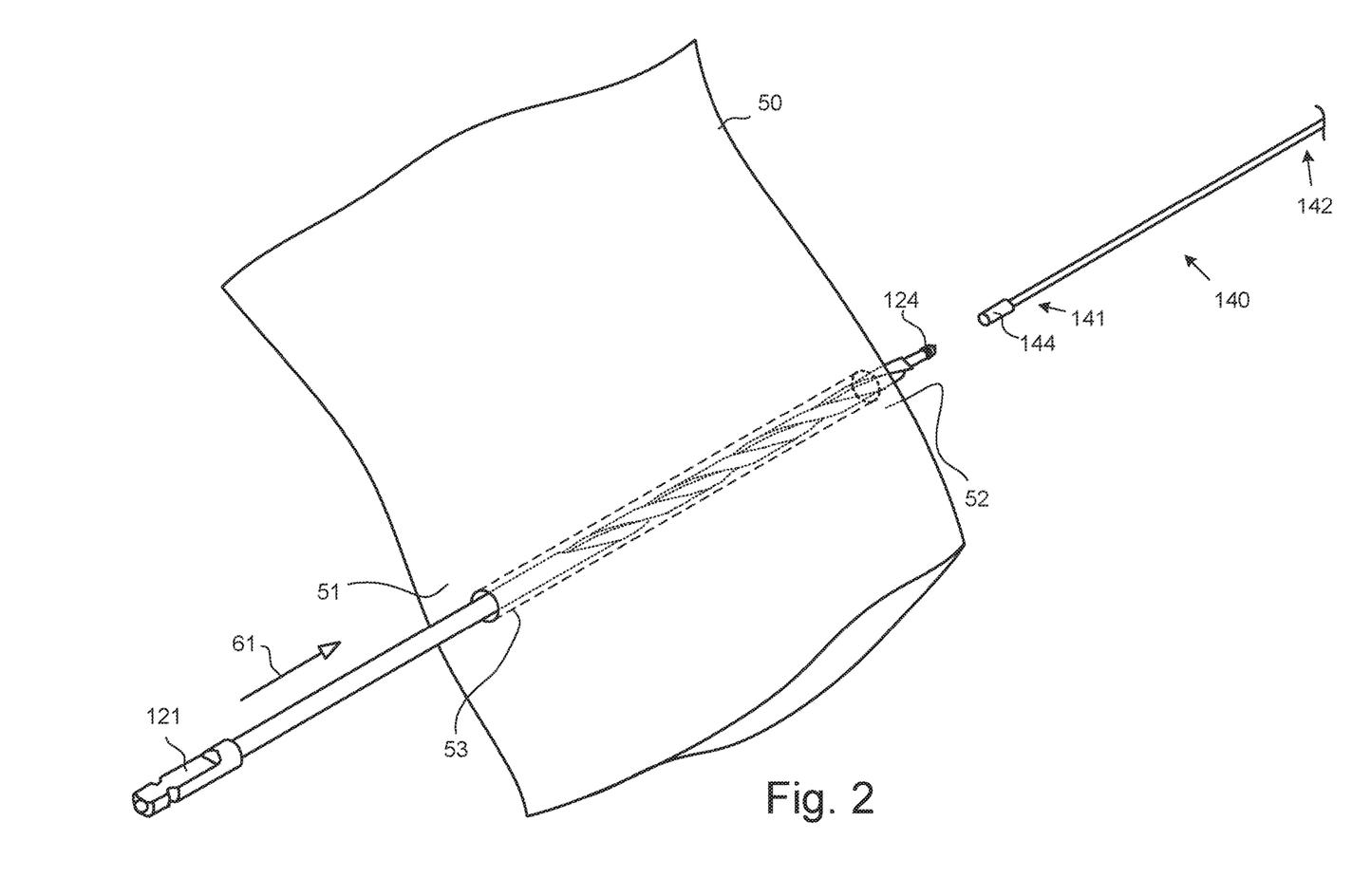
FIG. 2 is a perspective view of the hole-forming tool extending in a first direction through a pass-through hole in a bone, according to one embodiment.

FIG. 2 shows the hole-forming tool 120 extending in a first direction 61 through a pass-through hole 53 in a bone 50. The hole-forming tool 120 extends from a first side 51 of the bone 50 to a second side 52 of the bone 50. Once the pass-through hole 53 has been formed, the cable 140 may be coupled to the hole-forming tool 120 (as shown in FIG. 3A) to collectively pass the hole-forming tool 120 and the cable 140 through the pass-through hole 53.

Figure 3A:
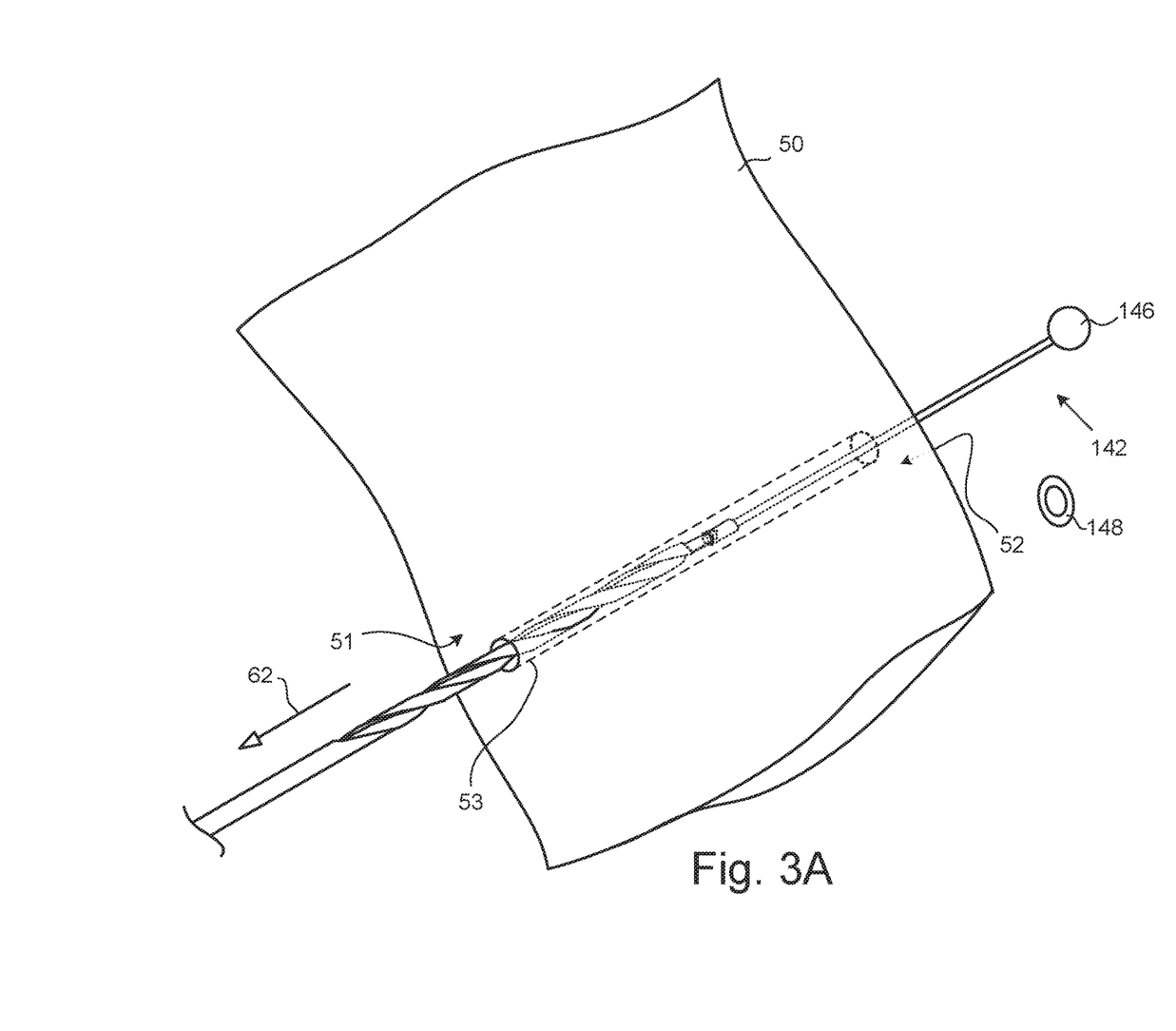
FIG. 3A is a perspective view of the hole-forming tool, with the cable coupled to the first connection feature of the hole-forming tool, being pulled in a second direction through the pass-through hole in the bone, according to one embodiment.

FIG. 3A shows the hole-forming tool 120 being pulled in a second direction 62 through the pass-through hole 53 in the bone 50 (e.g., from the second side 52 of the bone 50 to the first side 51 of the bone 50). With the second connection feature 144 of the first-end portion 141 of the cable 140 being coupled to the first connection feature 124 of the hole-forming tool 120, the cable 140 is pulled through the pass-through hole 53 along with the hole-forming tool 120. In other words, after the hole-forming tool 120 has drilled completely through the bone 50, and at least the first connection feature 124 of the hole-forming tool 120 is protruding from the pass-through hole 53 on the second side 52 of the bone 50, the cable 140 is coupled to the hole-forming tool 120 and subsequently pulled back through the pass-through hole 53 with the hole-forming tool 120.

Figure 3B:
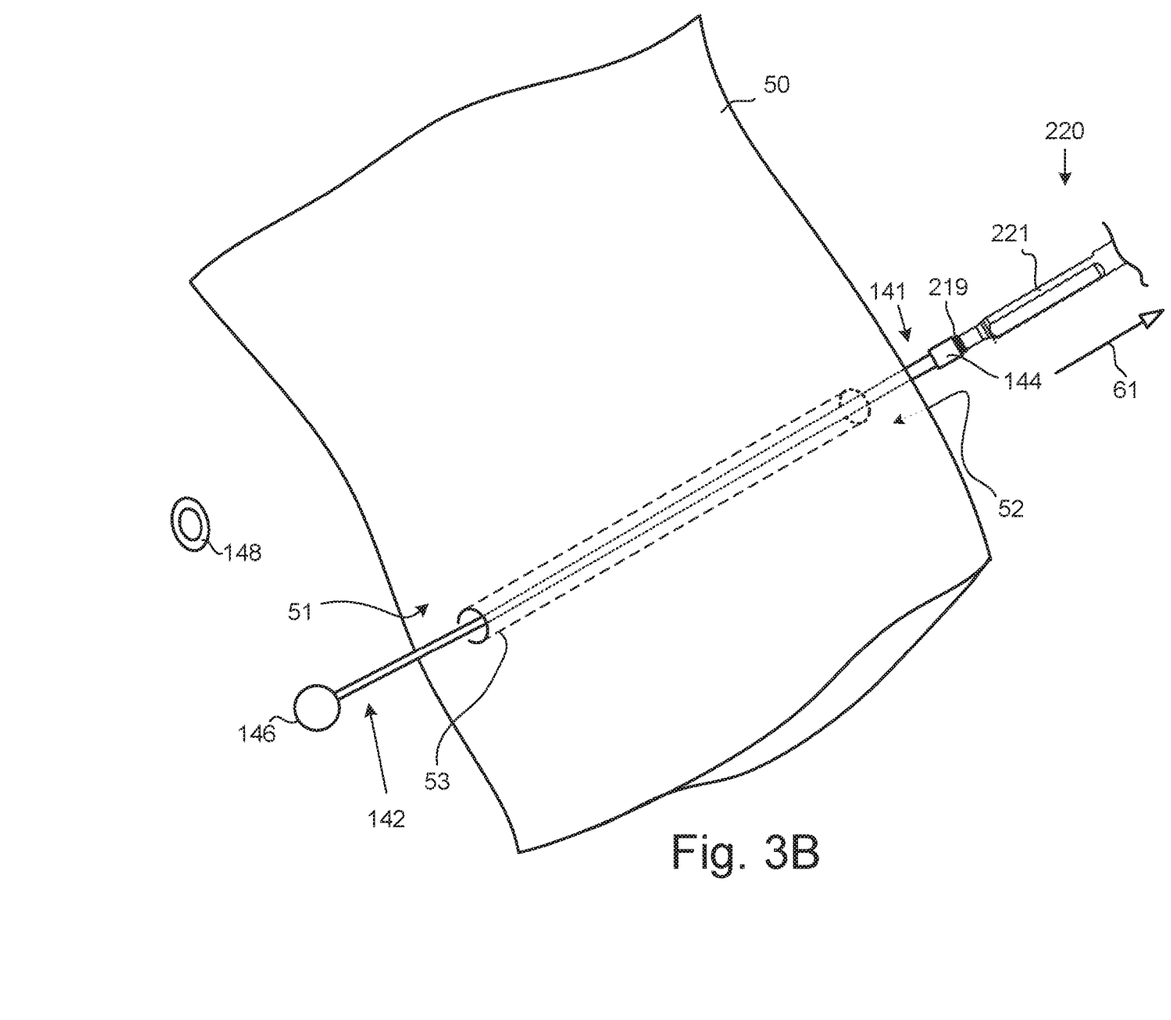
FIG. 3B is a perspective view of the hole-forming tool, with the cable coupled to the shank connection feature of the hole-forming tool, being pulled in the second direction through the pass-through hole in the bone, according to one embodiment.

In contrast to FIG. 3A, FIG. 3B shows the cable 140 being passed through the pass-through hole 53 in the first direction 61, which is opposite the second direction 62. In other words, FIG. 3B shows how the cable 140 can be passed through the pass-through hole 53 in the same direction the hole-forming tool 220 (FIG. 1B) was driven to form the pass-through hole 53. As introduced above with reference to FIG. 1B, according to one embodiment, the hole-forming tool 220 includes the shank connection feature 219 disposed at the end of the shank 221 of the hole-forming tool 220. In such an embodiment, the second connection feature 144 of the first-end portion 141 of the cable 140 can be coupled to the shank connection feature 219 of the hole-forming tool 220. In other words, after the hole-forming tool 220 has drilled completely through the bone 50, leaving at least a portion of the hole-forming tool 220 (e.g., the first connection feature 124) protruding from the pass-through hole 53 on the second side 52 of the bone 50, the drilling tool may be detached from the shank 221, thus leaving the shank connection feature 219 protruding from the pass-through hole 53 on the first side 51 of the bone 50. In one embodiment, the cable 140 is pre-attached to the shank connection feature 219. In other embodiments, the cable 140 may be coupled to the hole-forming tool 220 via the respective connection features 144, 219 and the hole-forming tool 220 and the cable may be collectively pulled through the pass-through hole 53.

After passing the cable 140 through the pass-through hole 53, the cable 140 can be tensioned to a measurable and adjustable tension, and maintained in tension by fixing retaining features to the cable 140 at opposing open ends of the pass-through hole 53. In some implementations, the pass-through hole 53 extends through two bone segments of a fractured bone such that tensioning the cable 140 to a measurable and adjustable tension in this manner causes the two bone segments to compress together with a measurable and adjustable compression. Moreover, because the cable 140 passes through the bone, as opposed to around the bone, the compression of the two bone segments is applied in one direction (e.g., unidirectionally) concentric with the cable 140, to more uniformly and evenly distribute the compressive load to the bone segments, as opposed to multiple directions when compression is applied by a cable passing around the bone.

In one embodiment, as an example only, the connection features 124, 219 of the hole-forming tool are threads that compliment and are threadably engageable with threads of the second connection feature 144 of the cable 140. The threads of the second connection feature 144 may be pass-by-threads, thereby enabling the cable 140 to rotate about its axis independent of the hole-forming tool 120 once the threads of the second connection feature 144 have been threaded beyond the threads of connection features 124, 219 so that the threads of the second connection feature 144 are disposed proximate a non-threaded portion 118 (as shown in FIG. 5B) of the hole-forming tool 120. In other words, the threads of the second connection feature 144, while no longer directly and threadably engaged with the threads of the connection features 124, 219 of the hole-forming tool 120, are still retained on the non-threaded portion 118 because the threads of the connection features 124, 219 act as a stop, thus allowing the hole-forming tool and the cable to rotate independently (e.g., rotate relative to each other) while still being coupled together.

Depending on the details of a specific surgical procedure, it may not be possible to pull the hole-forming tool through the pass-through hole 53 in one of the directions. For example, if the hole-forming tool is not able to be pulled backwards (i.e., in the second direction 62) through the pass-through hole 53 it just formed, the cable 140 may be connected to the shank connection feature 219 and the hole-forming tool may continue moving through the pass-through hole 53 in the first direction 61. Alternatively, if working space is relatively limited on the second side 52 of the bone 50, it may be difficult or impossible to pass the entire hole-forming tool through the pass-through hole 53, thus the cable 140 may be connected to the first connection feature 124 and the cable 140 and hole-forming tool 120 may be pulled backwards through the pass-through hole 53 in the second direction 62.

According to the embodiments depicted in FIGS. 3A and 3B, the second-end portion 142 of the cable 140 includes a retainer feature 146. The retainer feature 146 has a dimension that is larger than the diameter of the pass-through hole 53, thus prevent the retainer feature 146 from entering into or passing through the pass-through hole 53. In other words, the retainer feature 146 engages an opening of the pass-through hole 53 on the second side 52 of the bone 50 (FIG. 3A) or the first side 51 of the bone 50 (FIG. 3B).

In one embodiment, the retainer feature 146 is a spherical or rounded. In another embodiment, the retainer feature 146 resembles a flange or a washer. The retainer feature 146 may be integrated or permanently attached to the second-end portion 142 of the cable 140. For example, the retainer feature 146 may be swaged to the cable 140. In another embodiment, the retainer feature 146 may be detachably coupled to the cable 140, thus allowing for retainer features that have different shapes, dimensions, angles, etc. to be implemented. In another embodiment, the apparatus 100 may also include a washer 148 that further facilitates proper retaining engagement between the retainer feature 146 and the surface of the bone 50 adjacent the opening of the pass-through hole 53. In other words, the washer 148 may directly engage the surface of the bone 50 and the retainer feature 146 may be secured to, or at least engaged with, the washer 148.

In certain surgical procedures, the practitioner may need to tension the cable 140 in order to use the cable 140 to adequately hold and support the various tissues (e.g., bone tissue, soft-tissue) in a desired orientation. The retainer feature 146 enables the cable 140 to be tensioned by preventing the cable 140 from slipping through the pass-through hole 53.

Figure 4:
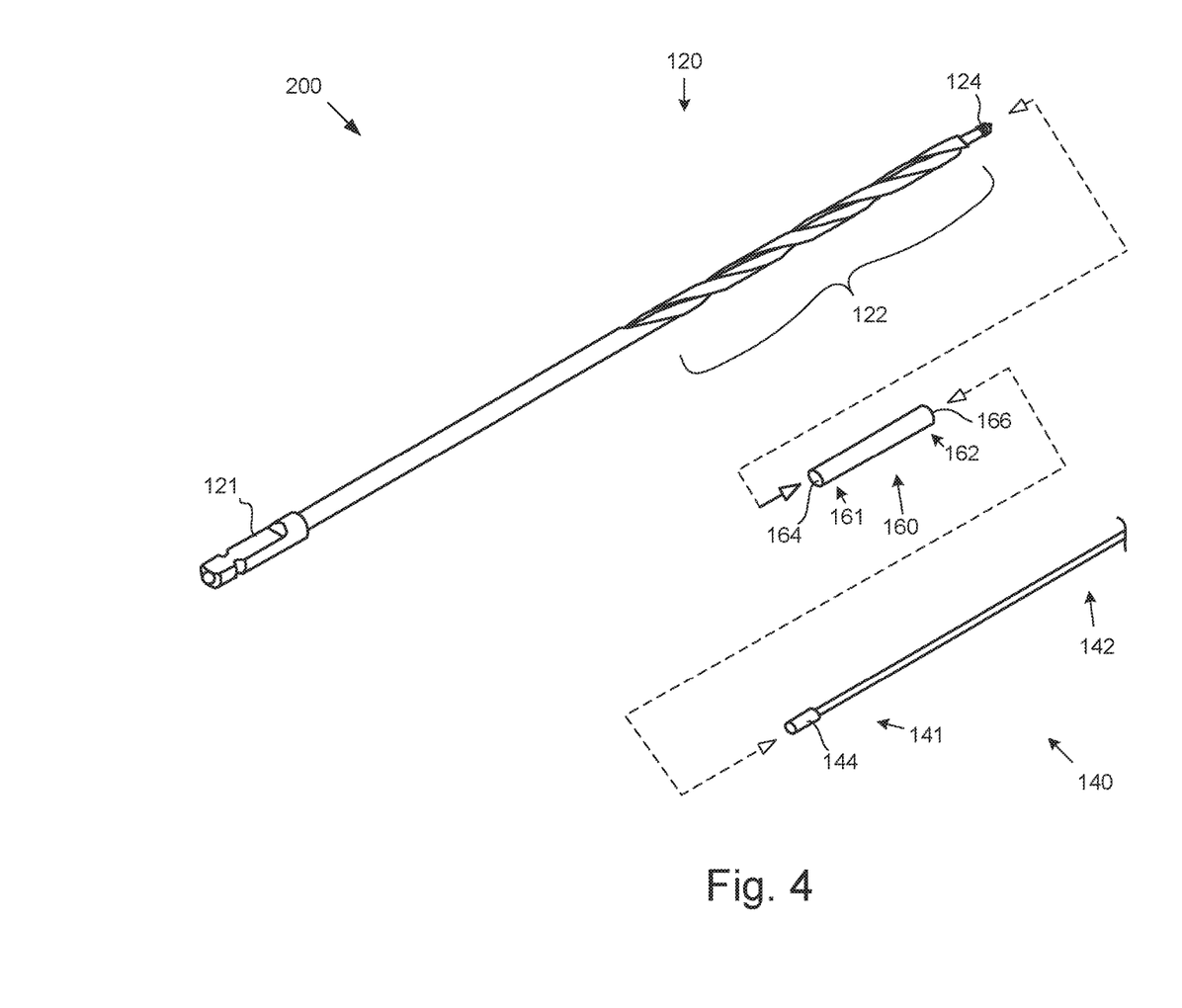
FIG. 4 is a perspective exploded view of the apparatus with a coupler, according to one embodiment.

FIG. 4 is a perspective exploded view of the apparatus 200 with the coupler 160, according to one embodiment. As introduced above, the coupler 160 has a proximal-end portion 161 and a distal-end portion 162. The proximal-end portion 161 has a third connection feature 164 and the distal-end portion 162 has a fourth connection feature 166. The third connection feature 164 is coupled to either the first connection feature 124 or the shank connection feature 219 and the fourth connection feature 166 is coupled to the second connection feature 144 of the first-end portion 141 of the cable 140.

The connecting structure of the respective complimentary connection features may include any of various connection elements. In other words, the connection features may include threads, clasps, tongue-and-groove elements, interference fit elements, magnets, and swage lock elements, among others. In one embodiment, the connection features 124, 219 on the hole-forming tool have a different connection structure than the second connection feature 144 of the cable 140, thus preventing the hole-forming tool from directly connecting to the cable 140. In such an embodiment, the third connection feature 164 of the coupler 160 has a connection structure that is complimentary to the connection features 124, 219 of the hole-forming tool while the fourth connection feature 166 has a connection structure that is complimentary to the second connection feature 144 of the cable 140, thus allowing otherwise incompatible connection features on the hole-forming tool and the cable 140 to be indirectly coupled together via the coupler 160

In one example, the connection features 124, 219 of the hole-forming tool have externally facing threads and the third connection feature 164 of the coupler 160 has internally facing threads that are threadably engageable with the externally facing threads of the hole-forming tool connection features 124, 219. In one embodiment, the third connection feature 164 of the coupler 160 has pass-by-threads, thereby enabling the coupler to rotate about its axis independent of the hole-forming tool once the threads of the third connection feature 164 have been threaded entirely through the threads of the first connection feature 124 or the shank connection feature 219. In another embodiment, the second connection feature 144 of the first-end portion 141 of the cable 140 has a non-threaded protrusion and the fourth connection feature 166 of the distal-end portion 162 of the coupler 160 has a complimentary non-threaded cavity such that the non-threaded protrusion of the second connection feature 144 is configured to be received into the non-threaded cavity of the fourth connection feature 166 via an interference fit.

In one embodiment, the coupler 160 facilitates a quick and easy connection between the hole-forming tool and the cable 140. For example, in certain surgical conditions it may be difficult to couple the cable 140 directly to the hole-forming tool 120 due to lack of space on one side of the bone or limited visibility on that side of the bone.

The coupler 160 may be made from various materials, including metals such as stainless steel and synthetics such as plastic, polymer, and composite material. The coupler 160 material may be flexible, resiliently flexible, or rigid. In one embodiment, the coupler 160 is disposable. In another embodiment, the coupler 160 may be sterilized for re-use. The coupler 160 may have an external cross-sectional dimension that is substantially uniform along the entire length of the coupler. In another embodiment, the external cross-sectional dimension of the coupler 160 may vary along its length. Also, while the cross-sectional shape of the coupler 160 is depicted as being circular (e.g., a cylindrical body), in other embodiments the coupler 160 may have a rectangular or polygonal cross-sectional shape. In one embodiment, the diameter of the coupler 160 is at least less than the diameter of the cutting portion 122 of the hole-forming tool, thus allowing the coupler to easily pass through the pass-through hole 53.

Figure 5A:
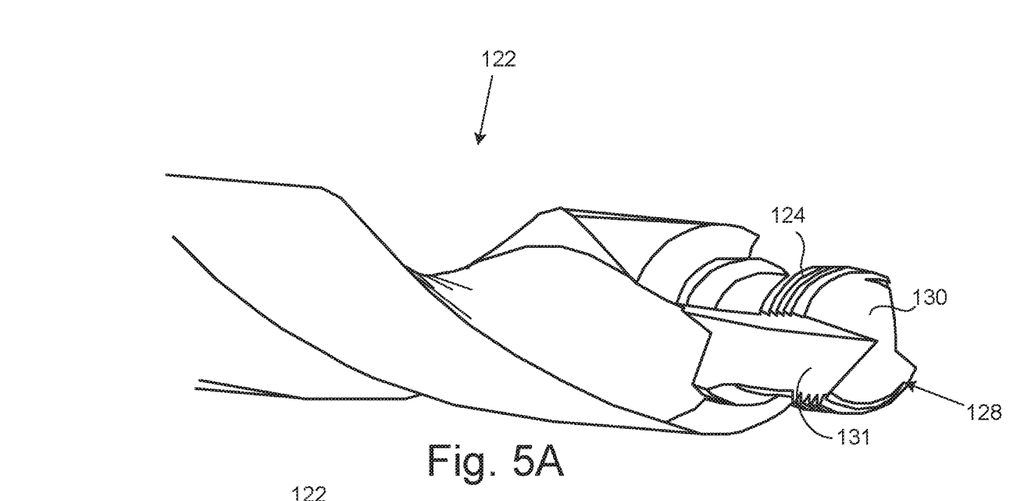
FIG. 5A is a perspective view the first connection feature of the hole-forming tool, according to one embodiment.
Figure 5B:
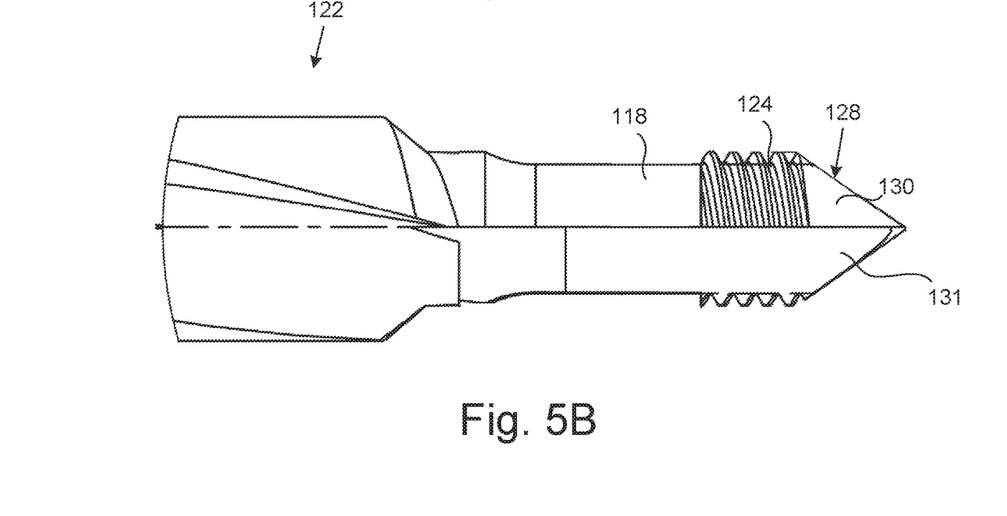
FIG. 5B is a side view of the first connection feature of the hole-forming tool, according to one embodiment.

FIG. 5A is a perspective view the first connection feature 124 of the hole-forming tool 120 and FIG. 5B is a side view of the first connection feature 124 of the hole-forming tool 120, according to one embodiment. The hole-forming tool 120 includes a second cutting portion 128. In other words, the first connection feature 124 is interposed between the first cutting portion 122 (described above) and the second cutting portion 128. The second cutting portion 128 includes a cutting tip 130 that has a diameter that is smaller than the diameter of the first cutting portion 122. In other words, the cutting tip 130 drills a guide hole and the first cutting portion 122 expands the guide hole to the size of the pass-through hole 53 shown in the figures. In one embodiment, the diameter of the second cutting portion 128 may be the same size or just larger than the diameter of the first connection feature 124. In other words, the first connection feature 124 may be slightly radially recessed relative to the second cutting portion 128, thus ensuring the guide hole/pilot hole is large enough to not damage the first connection feature 124 (e.g., threads). In the embodiment depicted in FIGS. 5A and 5B, the hole-forming tool may also include cutaway portions that further facilitate cutting and drilling through the bone 50.

Figure 6A:
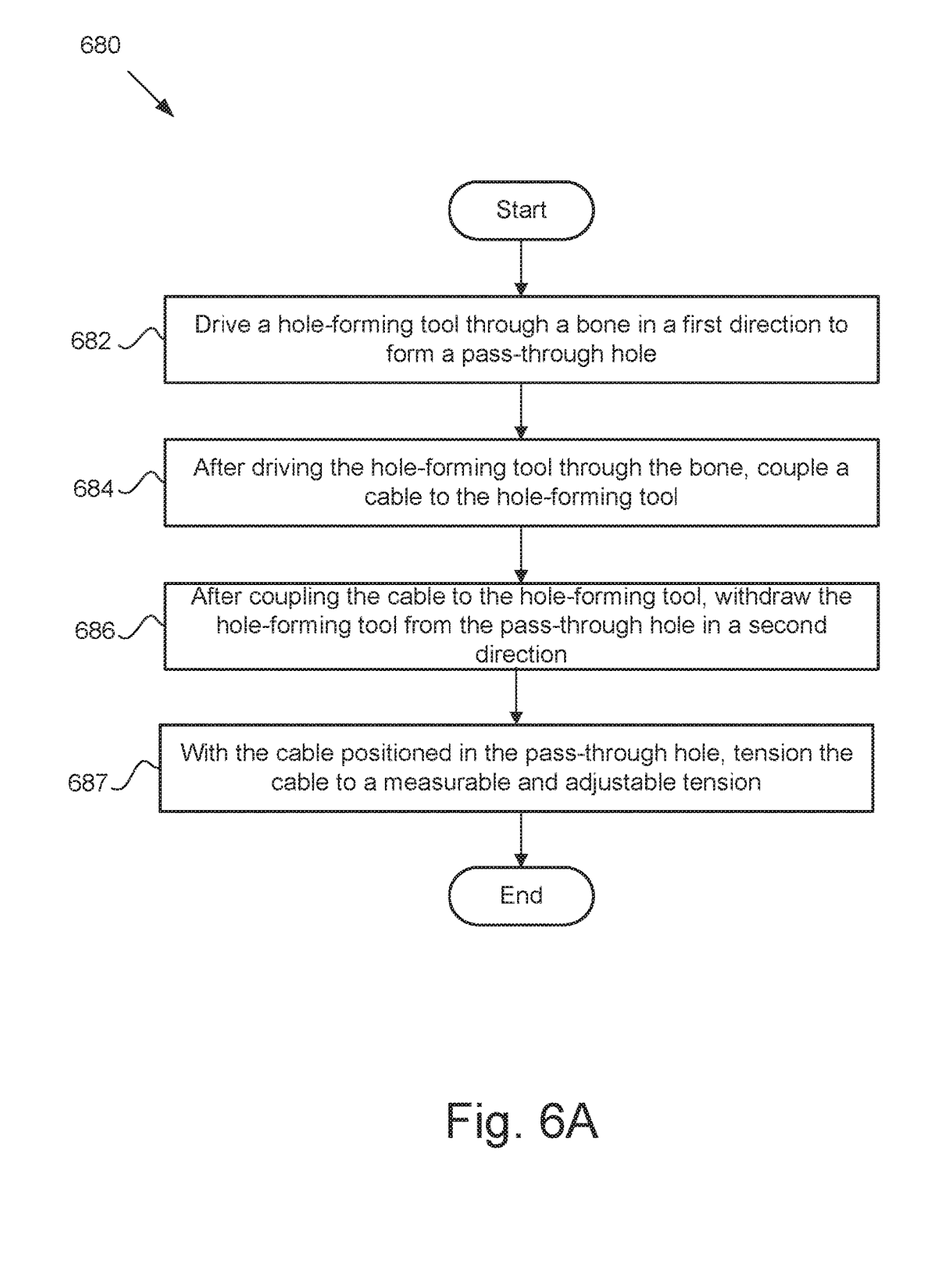
FIG. 6A is a schematic flowchart diagram of a method for passing cable through bone in the second direction, according to one embodiment.
Figure 6B:
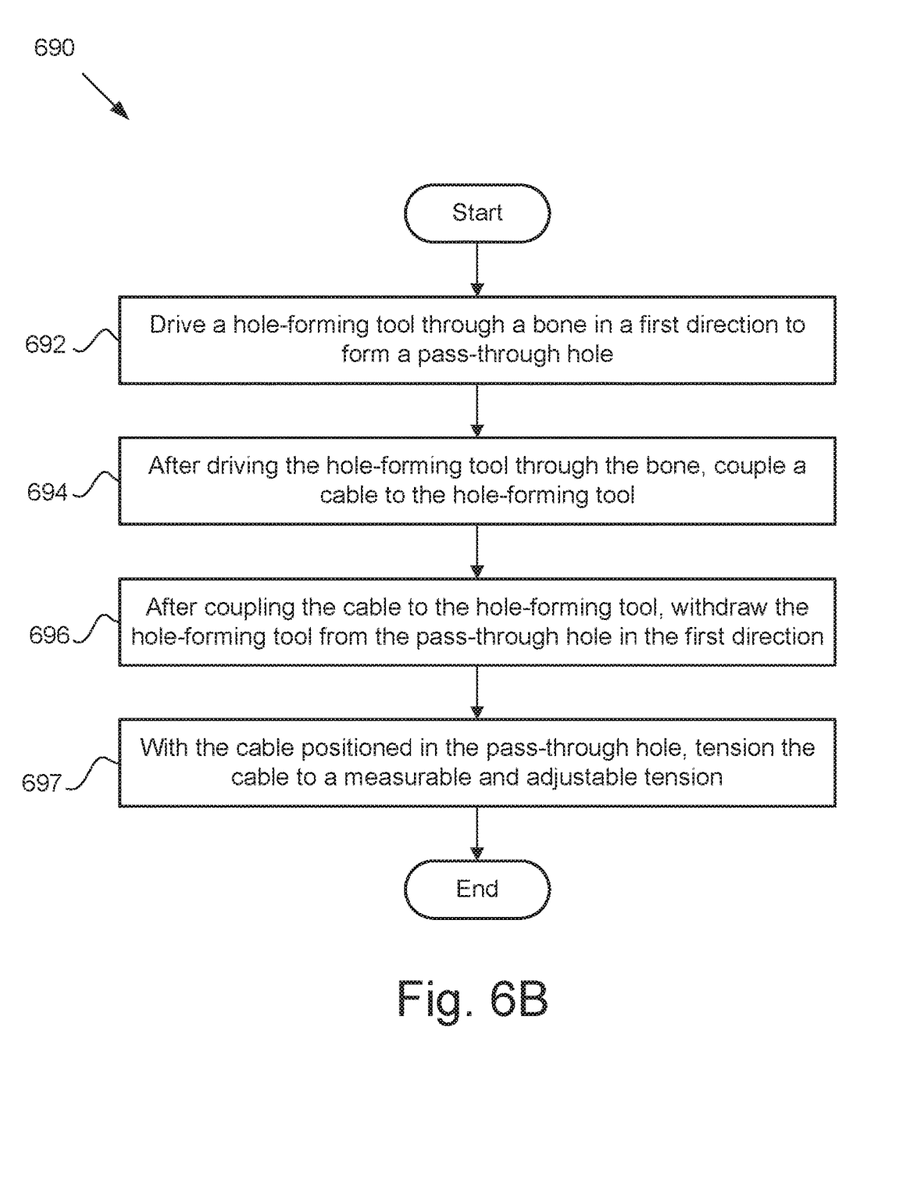
FIG. 6B is a schematic flowchart diagram of the method for passing cable through bone in the first direction, according to one embodiment.

FIG. 6A is a schematic flowchart diagram of a first method 680 for passing cable through bone in the second direction 62, according to one embodiment, and FIG. 6B is a schematic flowchart diagram of a second method 690 for passing cable through bone in the first direction 61, according to one embodiment. The first method 680 includes driving the hole-forming tool 120 through the bone in the first direction 61 to form a pass-through hole 53 extending from the first side 51 of the bone 50 to the second side 52 of the bone until at least the first connection feature 124 of the hole-forming tool 120 protrudes from the pass-through hole 53 on the second side 52 of the bone 50 at 682. The first method 680 further includes subsequently coupling the cable 140 to the hole-forming tool 120 via the first connection feature 124 of the hole-forming tool 120 and the second connection feature 144 of the cable 140 at 684 and then withdrawing the hole-forming tool 120 from the pass-through hole 53 in the second direction 62 opposite the first direction 61 to pull the cable 140 through the pass-through hole 53 such that at least a portion of the cable 140 protrudes from the first side 51 of the bone 50 at 686.

With the cable positioned in the pass-through hole, the method 680 further includes tensioning the cable to a measurable and adjustable tension at 687, to cause a measurable and adjustable compression of the bone by the cable in some implementations. In one embodiment, the method 680 may optionally include, after the cable is tensioned to a measurable and adjustable tension, releasing the tension in the cable and re-tensioning the cable, while positioned in the pass-through hole or otherwise, to the same or different measurable and adjustable tension. Releasing the tension in the cable may include unlocking a lock that is configured to maintain the cable in tension. The ability to release tension in a cable and subsequently re-tension the cable provides various advantages, such as, for example, facilitating re-use of the cable on other targeted areas of the body in one or more subsequent procedures, in some implementations, and adjustment to the tension or position of the cable on the same targeted area of the body in the same or a subsequent procedure, in other implementations.

Coupling the cable 140 to the hole-forming tool 120 may include coupling the hole-forming tool 120 directly to the coupler 160 via engagement between the first connection feature 124 of the hole-forming tool 120 and the third connection feature 164 of the proximal-end portion 161 of the coupler 160 and also coupling the coupler 160 directly to the cable 140 via engagement between the fourth connection feature 166 of the distal-end portion 162 of the coupler 160 and the second connection feature 144 of the first-end portion 141 of the cable 140. In another implementation, the step of withdrawing the hole-forming tool from the pass-through hole at 686 includes engaging the retainer feature 146 of the second-end portion 142 of the cable 140 with an opening of the pass-through hole 53 on the second side 52 of the bone 50. In one implementation, driving the hole-forming tool at 682 includes cutting the bone with the first cutting portion 122 of the hole-forming tool and the second cutting portion 128 of the hole-forming tool 120, with the second cutting portion 128 forming a pilot hole for the first cutting portion 122.

The second method 690 shown in FIG. 6B includes driving the hole-forming tool 220 through the bone 50 in the first direction 61 to form the pass-through hole 53 extending from the first side 51 of the bone 50 to the second side 52 of the bone 50, leaving at least the shank connection feature 219 of the hole-forming tool 220 protruding from the pass-through hole 53 on the first side 51 of the bone 50 at 692. The second method 690 subsequently includes coupling the cable 140 to the hole-forming tool 220 via the shank connection feature 219 of the hole-forming tool 220 and the second connection feature 144 of the cable 140 at 694 and then withdrawing the hole-forming tool 220 from the pass-through hole 53 in the first direction 61 to pull the cable 140 through the pass-through hole 53 such that at least a portion of the cable 140 protrudes from the second side 52 of the bone 50. With the cable positioned in the pass-through hole, the method 690 further includes tensioning the cable to a measurable and adjustable tension at 697, to cause a measurable and adjustable compression of the bone by the cable in some implementations. In one embodiment, the method 690 may optionally include, after the cable is tensioned to a measurable and adjustable tension, releasing the tension in the cable and re-tensioning the cable, while positioned in the pass-through hole or otherwise, to the same or different measurable and adjustable tension.

In one embodiment, coupling the cable 140 to the hole-forming tool 220 at 696 includes coupling the hole-forming tool 220 directly to the coupler 160 via engagement between the shank connection feature 219 of the hole-forming tool 220 and the third connection feature 164 of the coupler 160 and also coupling the coupler 160 directly to the cable 140 via direct engagement between the fourth connection feature 166 of the coupler 160 and the second connection feature 144 of the first-end portion 141 of the cable 140. In another implementation, withdrawing the hole-forming tool 220 from the pass-through hole 53 includes engaging a retainer feature 146 of the second-end portion 142 of the cable 140 with an opening of the pass-through hole 53 on the first side 51 of the bone 50.

In the above description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise.

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C; or some other suitable combination. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The subject matter of the present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. An apparatus for passing a cable through a pass-through hole in a bone, the apparatus comprising:
   a hole-forming tool comprising a shank, a cutting portion, and a first connection feature, wherein:
      the cutting portion is interposed between the shank and the first connection feature; and
      the shank is detachably coupleable to a driving tool; and
   a cable comprising a first-end portion having a second connection feature, wherein the cable is detachably coupleable to the hole-forming tool via the first connection feature of the hole-forming tool and the second connection feature of the first-end portion of the cable.

2. The apparatus of claim 1, further comprising a coupler comprising a proximal-end portion and a distal-end portion, wherein:
   the proximal-end portion comprises a third connection feature and the distal-end portion comprises a fourth connection feature;
   the hole-forming tool is detachably coupleable to the proximal-end portion of the coupler via engagement between the first and third connection features; and
   the distal-end portion of the coupler is detachably coupleable to the cable via engagement between the second and fourth connection features.

3. The apparatus of claim 2, wherein:
   the cutting portion of the hole-forming tool is a first cutting portion, wherein the hole-forming tool comprises a second cutting portion, the first connection feature being interposed between the first cutting portion and the second cutting portion; and
   a diameter of the of the first cutting portion of the hole-forming tool is comparatively larger than a diameter of the second cutting portion of the hole-forming tool.

4. The apparatus of claim 3, wherein the diameter of the first cutting portion of the hole-forming tool is larger than a diameter of the coupler.

5. The apparatus of claim 3, wherein the second cutting portion of the hole-forming tool comprises a cutting tip.

6. The apparatus of claim 2, wherein:
   the first connection feature of the hole-forming tool comprises externally facing threads; and
   the third connection feature of the coupler comprises internally facing threads threadably engageable with the externally facing threads of the first connection feature.

7. The apparatus of claim 2, wherein:
   the second connection feature of the first-end portion of the cable comprises a non-threaded protrusion;
   the fourth connection feature of the distal-end portion of the coupler comprises a non-threaded cavity; and
   the non-threaded protrusion of the second connection feature is configured to be received into the non-threaded cavity of the fourth connection feature via an interference fit.

8. The apparatus of claim 1, wherein a second-end portion of the cable has a retainer feature configured to prevent the second-end portion of the cable from passing through the pass-through hole in the bone.

9. The apparatus of claim 1, wherein the first connection feature of the hole-forming tool retains the second connection feature of the first-end portion of the cable on the hole-forming tool and allows the second connection feature of the first-end portion of the cable to rotate relative to the first connection feature of the hole-forming tool.

10. The apparatus of claim 1, further comprising a shank connection feature, wherein:
    the shank is interposed between the first connection feature and the cutting portion; and
    the second connection feature of the first-end portion of the cable is detachably coupleable to the hole-forming tool via one of the first connection feature and the shank connection feature.

11. The apparatus of claim 10, further comprising a coupler comprising a proximal-end portion and a distal-end portion, wherein:
    the proximal-end portion comprises a third connection feature and the distal-end portion comprises a fourth connection feature;

the hole-forming tool is detachably coupleable to the proximal-end portion of the coupler via engagement between the third connection feature and one of the first connection feature and the shank connection feature; and the distal-end portion of the coupler is detachably coupleable to the cable via engagement between the second and fourth connection features.

12. The apparatus of claim 11, wherein:

the cutting portion of the hole-forming tool is a first cutting portion, wherein the hole-forming tool comprises a second cutting portion, the first connection feature being interposed between the first cutting portion and the second cutting portion; and a diameter of the of the first cutting portion of the hole-forming tool is comparatively larger than a diameter of the second cutting portion of the hole-forming tool.

13. The apparatus of claim 12, wherein the diameter of the first cutting portion of the hole-forming tool is larger than a diameter of the coupler.

14. The apparatus of claim 11, wherein:

the first connection feature and the shank connection feature of the hole-forming tool comprise externally facing threads; and the third connection feature of the coupler comprises internally facing threads threadably engageable with the externally facing threads of the first connection feature and the shank connection feature.

15. The apparatus of claim 11, wherein:

the second connection feature of the first-end portion of the cable comprises a non-threaded protrusion;

the fourth connection feature of the distal-end portion of the coupler comprises a non-threaded cavity; and the non-threaded protrusion of the second connection feature is configured to be received into the non-threaded cavity of the fourth connection feature via an interference fit.

* * * * *